US008148118B2

(12) United States Patent
Goswami et al.

(10) Patent No.: US 8,148,118 B2
(45) Date of Patent: Apr. 3, 2012

(54) METHOD OF INDUCING CHIRALITY TO EPOXIDES USING 2,3:4,6 DI-O-ISOPROPYLIDENE-2-KETO-L-GULONIC ACID MONOHYDRATE

(75) Inventors: Amrit Goswami, Jorhat-6 (IN); Kuladip Sarma, Jorhat-6 (IN); Ajit Kumar Hazarika, Jorhat-6 (IN)

(73) Assignee: Council of Scientific & Industrial Research, New Delhi (IN)

( * ) Notice: Subject to any disclaimer, the term of this patent is extended or adjusted under 35 U.S.C. 154(b) by 298 days.

(21) Appl. No.: 12/626,843

(22) Filed: Nov. 27, 2009

(65) Prior Publication Data
US 2010/0136635 A1    Jun. 3, 2010

(30) Foreign Application Priority Data
Nov. 28, 2008    (IN) .......................... 2696/DEL/2008

(51) Int. Cl.
C12P 17/02    (2006.01)
C12N 9/20    (2006.01)
(52) U.S. Cl. ....................................... 435/123; 435/198
(58) Field of Classification Search .................. None
See application file for complete search history.

(56) References Cited

U.S. PATENT DOCUMENTS
3,855,227 A    12/1974    Den Hollander ............. 546/144
5,358,860 A    10/1994    Hager et al. ................... 435/123

FOREIGN PATENT DOCUMENTS
EP    1770094    4/2007

OTHER PUBLICATIONS

Adamo et al., "Epoxidation of Alkenes by Amine Catalyst Precursors: Implication of Aminium Ion and Radical Cation Intermediates," *J. Am. Chem. Soc.*, 122:8317, 2000.
Bjorkling et al., "Lipase-mediated formation of peroxycarboxylic acids used in catalytic epoxidation of alkenes," *J. Chem. Soc. Chem. Commun.*, 19:1301, 1990.
Bortolini et al., "Two-way enantioselective control in the epoxidation of alkenes with the keto bile acid—Oxone® system," *Tetrahedron*, 62:4482, 2006.
Boyd et al., "Chemical synthesis and optical purity determination of optically active 1,2-epoxyindan and alcohol products which are also derived from mammalian or microbial metabolism of indene or indanones," *J. Chem. Soc. Perkin Trans.* 1, 2767, 1982.
Bream, "Synthesis of the $\beta_2$ Agonist (*R*)-Salmeterol Using a Sequence of Supported Reagents and Scavenging Agents," *Org. Lett.*, 4:3793, 2002.
Buchanan et al., "A Short Stereoselective Synthesis of (R)-Salmeterol," *Synlett*, 12:1948, 2005.
Capdevila et al., "Cytochrome P-450 enzyme-specific control of the regio- and enantiofacial selectivity of the microsomal arachidonic acid epoxygenase," *J. Biol. Chem.*, 265:10865, 1990.

Chaterjee et al., "Asymmetric epoxidation of alkenes with *tert*-butyl hydroperoxide catalyzed by a novel chiral complex of manganese(III) containing a sugar based tridentate Schiff-base ligand," *Catalysis Commun.*, 8:1345, 2007.
Constable et al., "Key green chemistry research areas—a perspective from pharmaceutical manufacturers," *Green Chemistry*, 9:411, 2007.
Di Fabio et al., "The asymmetric synthesis of both enantiomers of eliprodil," *Bioorganic and Medicinal Chemistry Lett.*, 5:551, 1995.
Fu et al., "Pseudomonas oleovorans monooxygenase-catalyzed asymmetric epoxidation of allyl alcohol derivatives and hydroxylation of a hypersensitive radical probe with the radical ring-opening rate exceeding the oxygen-rebound rate," *J. Am. Chem. Soc.*, 113:5878, 1991.
Geller et al., "Novel conditions for the Juliá—Colonna epoxidation reaction providing efficient access to chiral, nonracemic epoxides," *Tetrahedron Lett.*, 45:5065, 2004.
Ho et al., "Fluorinated Chiral Secondary Amines as Catalysts for Epoxidation of Olefins with Oxone," *J. Org. Chem.*, 70:898, 2005.
Hoveyda, "Substrate-directable chemical reactions," *Chem. Rev.*, 93:1307, 1993.
Izumi et al., "Baker's yeast reduction of α-(alkoxycarbonylamino)acetophenones and Lipase-catalysed resolution of 2-(alkoxycarbonylamino)-1-arylethanols," *J. Chem. Tech. Biotech.*, 66:233, 1996.
Jarvie et al., "Enzymatic epoxidation of polybutadiene," *Chem. Commun.*, 177, 1998.
Kakei et al., "Catalytic Asymmetric Epoxidation of α,β-Unsaturated Esters Using an Yttrium-Biphenyldiol Complex," *J. Am. Chem. Soc.*, 127:8962, 2005.
Kamal et al., "Chemoenzymatic synthesis2 of both enantiomers of fluoxetine, tomoxetine and nisoxetine: lipase-catalyzed resolution of 3-aryl-3-hydroxypropanenitriles," *Tetrahedron: Asymmetry*, 13:2039, 2002. Kazuhide et al., "Asymmetric epoxidation of hydrocarbon olefins by *tert*-butyl hydroperoxide with molybdenum(VI) catalysts in the presence of optically active diols. Application to the asymmetric synthesis of (3S)-2,3-oxidosqualene," *Tetrahedron Lett.*, 20:3017, 1979.
Legros et al., "Urea-Hydrogen Peroxide/Hexafluoro-2-propanol: An Efficient System for a Catalytic Epoxidation Reaction without a Metal," *Eur. J. Org. Chem.*, 19: 3290, 2002.
Liu et al., "Effective and recyclable dendritic ligands for the enantioselective epoxidation of enones," *Tetrahedron: Asymmetry*, 17:750, 2006.
Lv et al., "Catalytic asymmetric epoxidation of chalcones under poly(ethylene glycol)-supported *Cinchona* ammonium salt catalyzed conditions," *Tetrahedron: Asymmetry*, 17:330, 2006.

(Continued)

*Primary Examiner* — Tekchand Saidha
*Assistant Examiner* — Younus Meah
(74) *Attorney, Agent, or Firm* — Fulbright & Jaworski L.L.P.

(57) ABSTRACT

The present invention relates to a recyclable method to prepare chirally pure epoxides directly from olefins using a novel chiral acid 2,3:4,6-di-O-isopropylidene-2-keto-L-gulonic acid monohydrate as chiral inducer and anhydrous hydrogen peroxide in the form of urea hydrogen peroxide adduct (UHP) as oxidant and lipase enzyme as catalyst. Under the influence of lipase, the chiral acid 2,3:4,6-di-O-isopropylidene-2-keto-L-gulonic acid monohydrate is converted to per-acid in situ by the oxidant urea hydrogen peroxide which in turn transfers oxygen to olefin inducing chirality to the product epoxide. Using this technique, important epoxide building blocks of different industrially important compounds can be prepared with good yield and moderate enantioselectivity. Chiral epoxidation of olefins with environment friendly catalytic system that can be recycled is highly desirable in the context of Green Chemistry for preparation of many industrially important compounds.

10 Claims, No Drawings

OTHER PUBLICATIONS

Marchi-Delapierre et al., "A new chiral diiron catalyst for enantioselective epoxidation," *Chem. Commun.*, 1166, 2007.

Margolin, "Enzymes in the synthesis of chiral drugs," *Enzyme Micro. Technology*, 15(4):266, 1993.

Marigo et al., "Asymmetric Organocatalytic Epoxidation of α,β-Unsaturated Aldehydes with Hydrogen Peroxide," *J. Am. Chem. Soc.*, 127:6964, 2005.

McGarrigle and Gilheamy, "Chromium- and Manganese-salen Promoted Epoxidation of Alkenes," *Chemical Review*, 105:1563, 2005.

Ohta and Tetsukawa, "Microbial epoxidation of long-chain terminal olefins," *J. Chem. Soc. Chem. Commun.*, 849. 1978.

Ortiz de Montellano and Grab, "Cooxidation of styrene by horseradish peroxidase and phenols: a biochemical model for protein-mediated cooxidation," *Biochemistry*, 26:5310, 1987.

Ortiz de Montellano et al., "Stereochemistry of cytochrome P-450-catalyzed epoxidation and prosthetic heme alkylation," *J. Biol. Chem.*, 258:4208, 1983.

Ortiz de Montellano et al., "Structure-mechanism relationships in hemoproteins. Oxygenations catalyzed by chloroperoxidase and horseradish peroxidase," *J. Biol. Chem.*, 262:11641, 1987.

Ortiz de Montellano et al., "Theoretical and experimental analysis of the absolute stereochemistry of cis-.beta.-methylstyrene epoxidation by cytochrome P450cam," *J. Am. Chem. Soc.*, 113:3195, 1991.

Peris et al., "Aspartate-Catalyzed Asymmetric Epoxidation Reactions," *J. Am. Chem. Soc.*, 129:8710, 2007.

Rossiter et al., "Asymmetric epoxidation provides shortest routes to four chiral epoxy alcohols which are key intermediates in syntheses of methymycin, erythromycin, leukotriene C-1, and disparlure," *J. Am. Chem. Soc.*, 103:464, 1981.

Sarma et al., "A novel method for the synthesis of chiral epoxides from styrene derivatives using chiral acids in presence of *Pseudomonas* lipase G6 [PSL G6] and hydrogen peroxide," *Tetrahedron*, 63:8735, 2007.

Schurig and Wistuba, "Asymmetric Microsomal Epoxidation of Simple Prochiral Olefins," *Angew. Chem. Int. Ed. (Engl.)*, 23:796, 1984.

Shi, "Organocatalytic Asymmetric Epoxidation of Olefins by Chiral Ketones," *Acc. Chem. Res.*, 37:488, 2004.

Smet et al., "Synthesis of 1,2-Epoxyoctane by *Pseudomonas oleovorans* During Growth in a Two-Phase System Containing High Concentrations of 1-Octene," *Applied and Environmental Microbiology*, 42:811, 1981.

Sterling and Dalton, "The fortuitous oxidation and cometabolism of various carbon compounds by whole-cell suspensions of *Methylococcus capsulatus* (Bath)," *FEMS Microbiology Letters*, 5:315, 1979.

Uehling et al., "Synthesis and Evaluation of Potent and Selective $\beta_3$ Adrenergic Receptor Agonists Containing Acylsulfonamide, Sulfonylsulfonamide, and Sulfonylurea Carboxylic Acid Isosteres," *J. Med. Chem.* 45:567, 2002.

Vachon et al., "Biphasic Enantioselective Olefin Epoxidation Using *Tropos* Dibenzoazepinium Catalysts," *J. Org. Chem.*, 70:5903, 2005.

Wistuba et al., "Cytochrome *P*-450-catalyzed asymmetric epoxidation of simple prochiral and chiral aliphatic alkenes: species dependence and effect of enzyme induction on enantioselective oxirane formation," *Chirality*, 1:127, 1989.

Yang et al., "Epoxidation reactions catalyzed by rat liver cytochromes P-450 and P-448 occur at different faces of the 8,9-double bond of 8-methylbenz[a]anthracene," *Proc. Natl. Acad. Sci USA*, 79:6802, 1982.

Yi et al., "Asymmetric epoxidation of α,β-unsaturated ketones catalyzed by silica-grafted poly-(1)-leucine catalysts," *Tetrahedron Lett.*, 46:5665, 2005.

Zhang et al., "Asymmetric olefin epoxidation with sodium hypochlorite catalyzed by easily prepared chiral manganese(III) salen complexes," *J. Org. Chem.*, 56;2296, 1991.

Zhang et al., "Enantioselective epoxidation of unfunctionalized olefins catalyzed by salen manganese complexes," *J. Am. Chem. Soc.*, 112:2801, 1990.

METHOD OF INDUCING CHIRALITY TO EPOXIDES USING 2,3:4,6 DI-O-ISOPROPYLIDENE-2-KETO-L-GULONIC ACID MONOHYDRATE

BACKGROUND OF THE INVENTION

1. Field of the Invention

The present invention relates generally to the field of chemical synthesis. More particularly, it concerns methods for preparation of chirally pure epoxide.

2. Description of Related Art

Epoxides are very important synthetic intermediates for variety of biologically active and other synthetic molecules. These are key intermediates for preparation of chirally pure β-amino alcohols used as β-blockers (*Enzyme Microb. Technology* 1993, 15, 266; *J. Med. Chem.* 2002, 45, 567; *Org. Lett.* 2002, 4, 3793; *Synlett* 2005, 12, 1948; *J. Chem. Tech. Biotech.* 1996, 66, 233), different antibiotics (*J. Am. Chem. Soc.* 1981, 103, 464), neuroprotective agents (*Bioorganic and Medicinal Chemistry Lett.* 1995, 5, 551), antidepressants (*Tetrahedron: Asymmetry* 2002, 13, 2039) apart from serving as important precursor for the production of a variety of natural and clinical products. It is for these reasons studies have been on the run for asymmetric synthesis of epoxides from olefins through chemical and biochemical means. Chiral epoxides whether produced from olefins or other sources have the advantage as electrophilic intermediates for stereochemical synthesis involving reactions with nucleophiles. The present invention relates to a new method of producing chiral induction to styrene oxides and its derivatives and other chiral epoxides from the corresponding olefinic compounds using 2,3:4,6-di-O-isopropylidene-2-keto-L-gulonic acid monohydrate, which is otherwise used in its ester form for racemic modification of optically active amines through formation of diastereomeric salts (U.S. Pat. No. 3,855,227, Den Hollander, Charles William). This approach can be used in efficient synthesis of members of a large family of chiral intermediates without the need to design custom chiral synthesis for each new compound. The method conforms to the Roundtable suggestion chalked out in the ACS and Global Pharmaceutical industries meet held during 2005 (*Green Chemistry*, 2007, 9, 411).

The prior art shows that preparation of various chiral epoxides from styrene derivatives and other olefinic compounds has been accomplished employing various strategies using chemical catalysts or biological catalysts.

A. Chemical Synthesis

1. Yian Shi; *Acc. Chem. Res.* 2004, 37, 488 and References Cited Therein.

Chiral ketones more particularly carbocyclic analogues of fructose of the structural formula '5' have been shown to be effective organocatalysts for asymmetric epoxidation of cis & trans olefins represented by the structural formula '3' wherein $R_1$ is selected from the group consisting of alkyl, alicyclic, aryl, $R_2$ is selected from the group consisting of H, alkyl, and $R_3$ is selected from the group consisting of H, alkyl, allyl, carboxylic, etc.

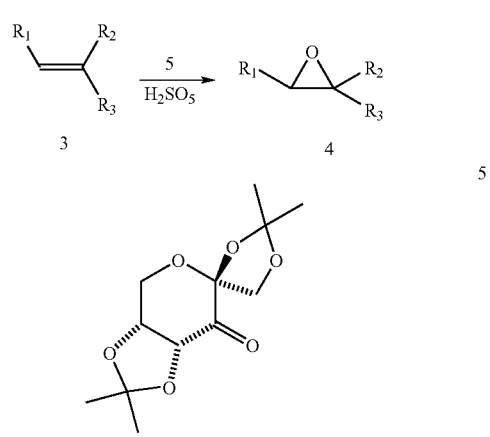

The disadvantage of this method is that it is highly pH dependent and the catalyst undergo decomposition through Baeyer-Villiger oxidation in presence of oxone.

2. C. Marchi-Delapierre, A. Jorge-Robin, A. Thibon and S Menage; *Chem. Commun.*, 2007, 1166.

Different olefins including electron deficient systems, undergo epoxidation at 0° C. in presence of a per-acid under the catalytic influence of dinuclear chiral complex $Fe_2O(bis PB)_4(X)2(ClO_4)_4$ ($X=H_2O$ or $CH_3CN$) '8' whereby a moderate enantioselectivity (9-63%) and yield were achieved.

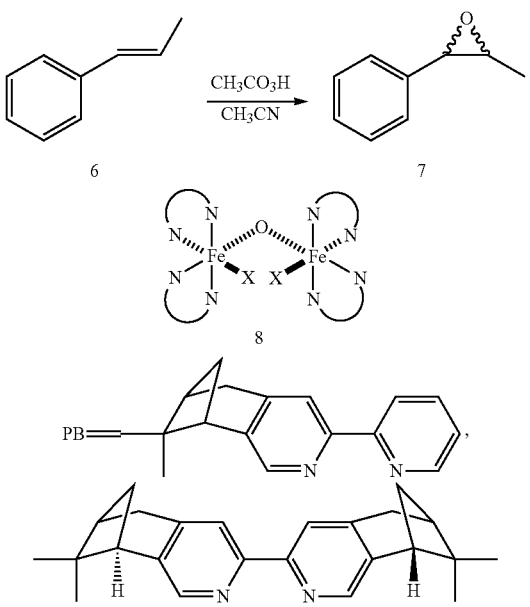

The disadvantage is that per acid used is expensive and unstable and the iron catalyst is to be specially designed.

3. E. M. McGarrigle and Declan G. Gilheamy; *Chemical Review*, 2005, 105, 1563.

A number of chromium and manganese metal salen complex represented by the general structural formula '9' wherein 'M' represents chromium or manganese have been reported to produce chirally pure epoxides (ee, 50-90%) from different substituted and unsubstituted olefins in presence of sodium hypochlorite oxidant.

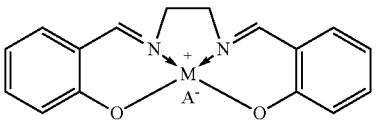

M = Cr or Mn
A = Counter ion

However, the catalyst is required to be specially designed and possesses environmental problems.

4. Hua Yi, G Zou, Q. Li, Q Chen, J. Tang and M.-Y. He; *Tetrahedron Lett.*, 2005, 46, 5665.

α/β-Unsaturated ketones represented by the structural formula '10' in which '$R_1$' consists of Ph, p-MeOC$_6$H$_4$, p-O$_2$NC$_6$H$_4$, o-MeOC$_6$H$_4$, o-EtOC$_6$H$_4$, p-ClC$_6$H$_4$ and '$R_2$' consists of Ph, o-MeOC$_6$H$_4$, p-ClC$_6$H$_4$ etc. undergo Julia-Colonna asymmetric epoxidation in the olefinic bond in presence of silica grafted poly-(L)-leucine catalyst and hydrogen peroxide with moderate to good enantioselectivity.

Scheme 4

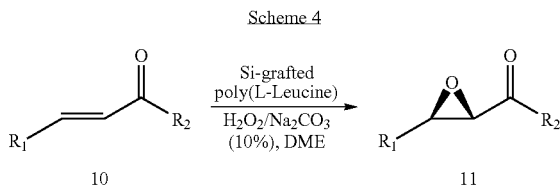

The disadvantage of this method is that it is limited to α,β-unsaturated systems only.

5. A. H. Hoveyda; *Chem. Rev.*, 1993, 93, 1307.

In this report olefinic compounds or chiral olefinic compounds having scope for specific binding with per-acid has been described. However, per-acid as such is expensive and unstable and unsafe for handling.

6. D. Chaterjee, S. Basak, A. Riahi and J. Muzart; *Catalysis Commun.* 2007, 8, 1345.

Chaterjee et. al. developed one catalyst Mn$^{III}$[(TDLi$^+$)(PIC)(H$_2$O)] represented by the structural formula '12' where TDLi stands for N-3,5-di-(t-butyl) salicylidine-D-glucosamine and PIC stands for picolinate in presence of which different styrene derivatives, methylcyclohexene, 1,2-dihydronaphthalene were transformed into chirally pure epoxides using t-butylhydroperoxide oxidant. The enantioselectivity and product yield have been found to be 52-68% and 8-54% respectively.

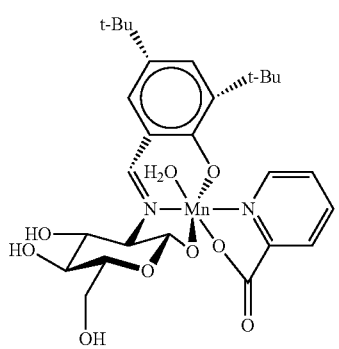

From the environmental aspect point of view, the yield and also the enantioselectivity achieved above, the use of the metal complex catalyst is not desirable.

7. H. Kakei, R. Tsuji, T. Ohshima and U. Shibasaki; *J. Am. Chem. Soc.*, 2005, 127, 8962.

This method describes chiral epoxidation of α/β-unsaturated methyl ester with good yield (62-97%) and enantioselectivity (89-99%) in presence of yttrium-biphenyldiol complex represented by the structural formula '13' and t-butylhydroperoxide.

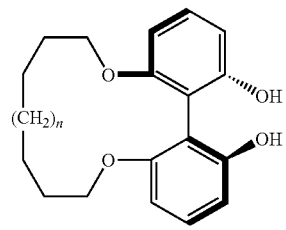

However, the complex catalyst is not environment friendly.

8. C.-Y. Ho, Y.-C Chen, M.-K Wong and D. Yang; *J. Org. Chem.* 2005, 70, 898.

Here in this method asymmetric epoxidation of various olefins has been reported in presence of different chiral cyclic secondary amines represented by the structural formula '16' under the oxidizing influence of oxone wherein R represents phenyl, p-tolyl, 1-naphthyl, 2-naphthyl, 4-phenylphenyl, 2,4-difluorophenyl, 3,5-di(trifluoromethyl)phenyl, R1=F, OH, OMe, R2=H, F and observed that amines having fluorine substituent at the -position relative to amine center has been found to give highest enantiomeric excess of 61% with 92% yield.

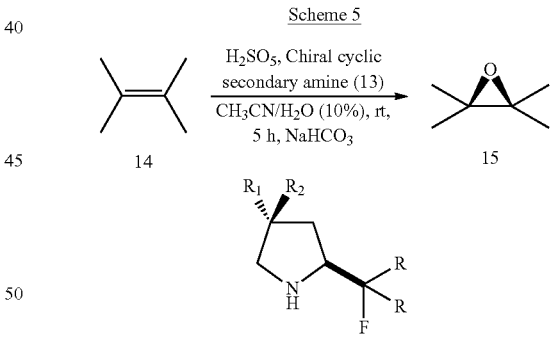

The drawback of this method is that the catalyst used is not eco-friendly and is not recyclable.

9. J. Vachon, C. Perollier, D Monchaud, C. Marsol, K. Ditrich and J. Lacour; *J. Org. Chem.* 2005, 70, 5903.

Vachon et. al. reported a catalytic system chiral iminium TRISPHAT [tris (tetrachlorobenzenediolato)phosphate(V)] salt combining a diphenylazepinium core represented by the structural formula '17' wherein $R_1$ & $R_2$ consists of H, alkyl, aryl group, chiral exocyclic appendages and a lipophilic counterion for biphasic chiral epoxidation of olefins of the formula '18' in which $R^1$ represents H, alkyl, aryl, $R^2$ represents H, alkyl, phenyl, naphthyl and $R^3$ represents phenyl, $R^2$=$R^3$=—(—C$_6$H$_4$(CH$_2$)$_2$— or $R^2$=$R^3$=—(CH$_2$)$_6$—.

From the cost and environmental point of view the catalysts is expensive, is to be specially designed and not friendly.

Scheme 6

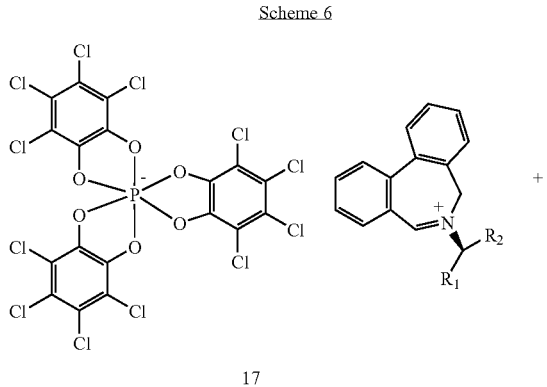

10. M. Marigo, J. Franzen, T. B. Poulsen, W. Zhuang and K. A. Jorgensen; *J. Am. Chem. Soc.*, 2005, 127, 6964.

This is an attractive method for asymmetric epoxidation of α,β-unsaturated aldehyde with $H_2O_2$, t-BuOOH or UHP in presence of chiral bisaryl silyl protected pyrrolidine '22' to have enantiomeric excess and diasteriomeric ratio to be more than 92 and 93:7.

Scheme 7

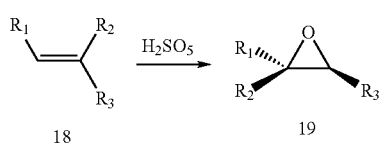

However the method is limited to α,β-unsaturated aldehyde only.

11. O. Bortolini, G. Fantin, M. Fogagnolo and L. Mari, *Tetrahedron*, 2006, 62, 4482.

Few 3-keto bile acid derivatives '23' have been evaluated in the asymmetric epoxidation of unfunctionalized olefins represented by the structural formula '1' in which $R_1$ consists of Ph, Tolyl, $R_2$ consists of H, methyl, $R_3$ consists of H, methyl, phenyl or '1' represents 1,2-dihydronaphthalene with oxone up to 98% ee has been achieved by this method.

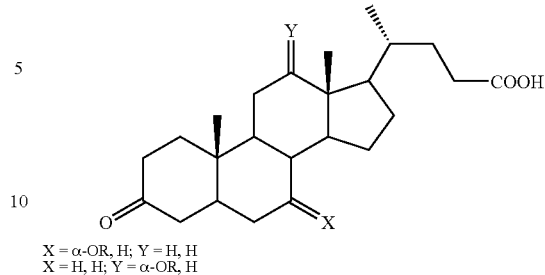

X = α-OR, H; Y = H, H
X = H, H; Y = α-OR, H

However, the catalyst availability is limited.

12. T. Geller, A. Gerlach, C. M. Kruger and H. Christian Militzer; *Tetrahedron Lett.*, 2004, 45, 5065.

This is an improvement of Julia-Colonna epoxidation of α,β-unsaturated ketone upon addition of a phase transfer catalyst yielding chiral, nonracemic epoxy ketones. The reaction is treatment of α,β-unsaturated ketone with $H_2O_2$ and poly L-leucine '26' in presence of tetrabutyl ammonium bromide (TBAB) as phase transfer catalyst that triggers acceleration of the reaction with 99% convertion and 94% enantiomeric excess.

Scheme 8

As stated, the reaction is limited to α,β-unsaturated system.

13. X. Liu, Y. Li, G. Wang, Z. Chi, Y. Wu and G. Zhao; *Tetrahedron: Asymmetry*, 2006, 17, 750.

α,β-Unsaturated ketones can also be epoxidized under mild protocol using chiral pyrrolidinyl methanol '27' as dendritic catalysts and t-butylhydroperoxide as oxidant.

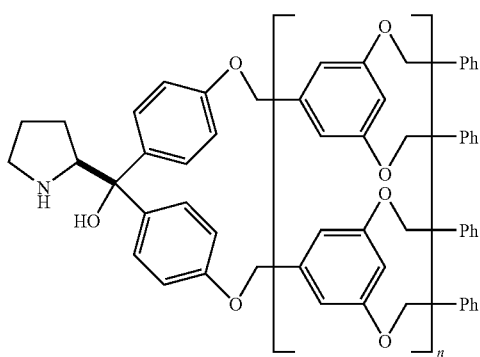

27

But the catalyst design is troublesome.

14. W. Zhang, J. L. Loebach, S. R. Wilson, E. N. Jacobsen; *J. Am. Chem. Soc.,* 1990, 112, 2801 and W. Zhang, E. N. Jacobsen; *J. Org. Chem.,* 1991, 56, 2296.

Here it is used (Salen) manganese complex '28' for enantioselective epoxidation of unfunctionalized olefins using NaOCl with 86% yield.

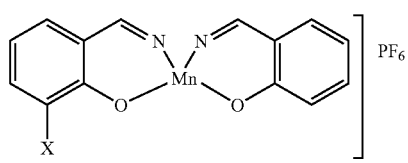

28

The catalyst is however not environment friendly.

15. Kazuhide Tani, Masayoshi Hanafusa, Sei Otsuka; *Tetrahedron Lett.,* 1979, 20, 3017.

Prochiral squalene has been chirally epoxidized with t-BHP and Mo (VI) catalysts in presence of optically active diols.

Scheme 9

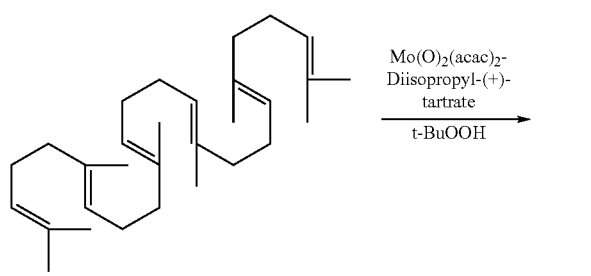

29

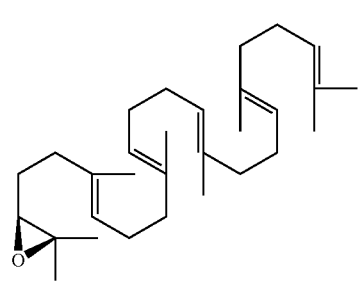

30

However, use of metal complex catalyst is not desirable.

16. J. Lv, X. Wang, J. Liu, L. Zhang and Y. Wang; *Tetrahedron: Asymmetry,* 2006, 17, 330.

Chiral epoxidation with 86% ee and 54-96% yield has been achieved using dimeric cinchonine, chinconidine and quinine anchoring to long linear PEG chain '31'.

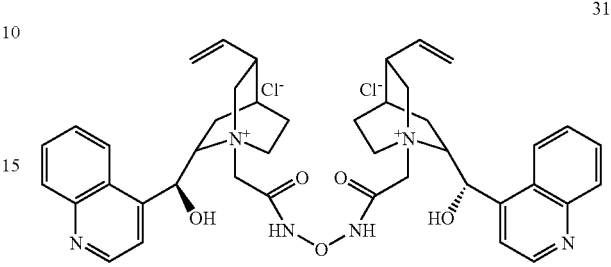

31

However, the catalyst availability is poor.

17. G. Paris, C. E. Jacobsche and S. J. Miller; *J. Am. Chem. Soc.,* 2007, 129, 8710.

This is another report of epoxidation using organic catalyst aspertate derivatives '32' having a peptide sequence through per-acid formation of aspertic carboxylic group with hydrogen peroxide in presence of either 4-N,N-dimethyl amino pyridine (DMAP or NMO with 76-89% ee and 80-95% isolated yield.

32

18. J. Legros, B. Crousse, D. Bonnet-Delpon and J.-P. Begue; *Eur. J. Org. Chem.,* 2002, 3290.

This is a report for achiral epoxidation of olefin using fluoroketone '33' as catalyst in presence of UHP in hexafluoro-2-propanol with good yield.

33

However, no chiral purity is achieved in the products.

19. M. F. A. Adamo, V. K. Agarwal and M. A. Sage; *J. Am. Chem. Soc.,* 2000, 122, 8317.

Agarwal et. al. reported another chiral epoxidation of olefins using amine catalyst more particularly chiral pyrrolidine derivative '34' and found to be better in yield and enantioselectivity compared to methyl trioxorhenium catalyst (MTO).

Scheme 10

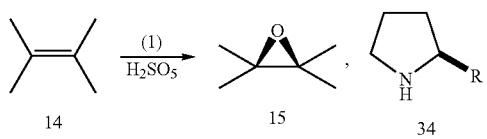

20. F. Bjorkling, S. E. Godtfredsen and O. Kirk; *J. Chem. Soc. Chem. Commun.*, 1990, 1301.

Bjorkling et. al reported the preparation of different epoxides acyclic and cyclic olefins using a fatty acid such as octanoic acid as oxygen carrier through in situ formation of its per-acid with hydrogen peroxide under the catalytic influence of lipase from different species with moderate to good yields. However no chirally pure could be isolated from this method.

21. K, Sarma, N Bhati, N Borthakur and A. Goswami, *Tetrahedron*, 2007, 63, 8735.

In this method chirally pure epoxide preparation from different olefins was reported using Urea-Hydrogen peroxide adduct and N-2,4-dinitrophenyl-L-proline in presence of lipase from Pseudomonas species G6 [PSLG6] with good yield and enantiomeric excess.

B. Enzyme Catalysis

Biological catalysts have been employed for epoxidation using pure enzyme or whole cell microbes. Oritg de Montellano et al.; *J. Am. Chem. Soc.*, 1991, 113, 3195; D. R. Boyd, N. D. Sharma and A. E. Smith; *J. Chem. Soc. Perkin Trans.* 1, 1982, 2767 and V. Schurig, D. Wistuba; *Angew. Chem. Int. Ed. (Engl.)*, 1984, 23, 796.

1. Using Cytochrome P-450

Cytochrome P-450 monooxygenase family has been used as epoxidation catalysis both with purified enzymes isolated from mammalian, microbial and plant sources and with partially purified liver microsomal preparation. The stereochemical course and the enantioselectivity of the P-450 reactions have been examined in some instances.

Wislocki and Lu.; *Proc. Natl. Acad. Sci. USA* 79, 1982, 6802. In this study the epoxidation of 8-methyl benz[a]anthracene has been reported using Cytochrome P-450 and P-448 and showed epoxidation at different faces of 8,9-double bond.

P. R. Ortiz de Montellano, B. L. Mangold, C. Wheeler, K. L. Kunze and N, O. Reich; *J. Biol. Chem.*, 1983, 258, 4208. Octene on epoxidation with Cytochrome P-450 gave S(−) enantiomer of the epoxide formed in the little excess over the R(+) isomer. Thus ee is poor.

2. Liver Microsomes

D. Wistuba, H.-P. Nowotny, O. Trager, V. Schurig; *Chirality*, 1989, 1, 127. Partial enantioselectivity (50% ee) has been observed in aliphatic alkene epoxides by liver microsomes. Since Cytochrome P-450 needs continuous supply of cofactors NADH such enzymes are not suitable for large scale synthesis.

3. Other Enzymes

J. H. Capdevila, A. Karara, D. J. Waxman, M. V. Martin, J. R. Falck and F. P. Guenguerich; *J. Biol. Chem.* 1990, 265, 10865. Methymoglobin and metmyoglobin catalyse the hydrogen peroxide depended oxidation of styrene to styrene oxide and benzaldehyde but with no enantiomeric excess.

4. Horseradish Peroxidase

P. R. Ortiz de Montellano, L. A. Grab; *Biochemistry*, 1987, 26, 5310. HR peroxidase is capable of catalyzing the oxidation of styrene when supplemented with hydrogen peroxide and oxidizable phenol. The key features of the reactions involve first the oxidation of the phenol to a free radical which in turn reacts with molecular oxygen to generate the peroxy radical. The peroxy radical then reacts with styrene to form the epoxide.

The problem encountered with these catalysts is that availability is limited.

5. By Chloroperoxidase

P. R. Ortiz de Montellano, Y. S. Choe, G. DePillis and C. E. Catalano; *J. Biol. Chem.*, 1987, 262, 11641. (i) Chloroperoxidase (CPO) and Cytochrome P-450 function similarly in the epoxidation and N-demethylation reactions. However, CPO utilizes $H_2O_2$ whereas the P-450 utilize molecular oxygen and require a regenerable reducing reagent usually NADH. The CPO and $H_2O_2$ oxidize styrene to styrene oxide and phenylacetyldehyde showed that trans epoxide is the major product.

L. P. Hager, E. J. Allan; U.S. Pat. No. 5,358,860, 1994. Here in this report olefin have been shown to epoxidize with $H_2O_2$ at pH 5 with good yield and 97% enantiomeric excess. But, due to very high cost of the enzyme and limited availability, the process is less meritorious.

A. W. P. Jarvie, N. Overton and C. B. St Pourcain; *Chem. Commun.*, 1998, 177. In this report epoxidation of phenylpolybutadiene has been reported to be done by Immobilized lipase and $H_2O_2$ in presence of acetic acid where 1,4-trans and 1,4-cis epoxy phenyl polybutadiene formed leaving behind 1,2-vinyl group in $CH_2Cl_2$ with poor yield (21-31%).

Dr. F. A. I. Vidal; N. Nieto Alonso; Dr. P. Molar Porqueras; European patent, EP 1770094. Here in this patent electron deficient alkenes have been reported to be epoxidized by dioxirane chiral ketone generated from oxone starting from D-fructose.

C. By Cell Cultures

1. H. Ohta and H. Tetsukawa; *J. Chem. Soc. Chem. Commun.*, 1978, 849.

In this report, conversion of alkenes viz. hexadec-1-ene to R(+) epoxide by whole cell culture of microorganism from *Coryniebacterium equi* has been studied.

2. D. I. Sterling and H. Dalton; *FEMS Microbiology Letters*, 1979, 5, 315.

Stirling and Dalton have shown that whole cell cultures of *Methylococcus Capsulatus* (Bath) are capable of converting ethylene, propylene, 1-butene and cis and trans-2-butene to epoxides when supplied with formaldehyde as co-substrate.

3. M.-J. D E Smet, H. Wynberg and B. Witholt; *Applied and Environmental Microbiology*, 1981, 42, 811.

D E Smet et. al. have shown that under optimum conditions, resting and growing cultures of *Pseudomonas oleovarans* convert 1-octene to 1,2-epoxyoctane.

4. H. Fu, M. Newcomb, C. H. Wong; *J. Am. Chem. Soc.*, 1991, 113, 5878.

In this report, Fu et. al. have shown that *Pseudomonas oleovarans* cultures were unable to oxidize internal olefins and distributed terminal olefins.

In short, it may be noted that despite substantial efforts throughout the world, to have benign method for epoxidation of olefins, several lacunae are therein and needs extensive work for eco-friendly epoxidation of olefins using organic or bioorganic catalysts.

SUMMARY OF THE INVENTION

The main objective of the invention is to provide a novel chiral epoxidation route from the olefins using urea hydrogen peroxide and chiral acid 2,3:4,6-di-O-isopropylidene-2-keto-L-gulonic acid monohydrate in presence of lipase.

Another objective of the invention is to provide a recyclable catalytic system for chiral epoxidation of olefins using chiral 2,3:4,6-di-O-isopropylidene-2-keto-L-gulonic acid monohydrate and immobilized lipase with urea hydrogen peroxide adduct as oxidant.

Yet another objective of the present invention is to provide a recyclable catalytic method for chiral epoxidation of olefins using a chiral acid 2,3:4,6-di-O-isopropylidene-2-keto-L-gulonic acid monohydrate from natural chiral pool carbohydrate.

Accordingly the present invention provides a process for preparation of chiral epoxy compounds of general formula 2 wherein

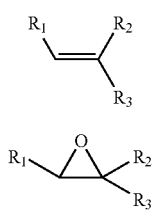

$R_1$ represents Me, Et, Ph, 4-(HO)$C_6H_4$, 3-($NO_2$)$C_6H_4$, 4-(Cl)$C_6H_4$, $R_2$ represents H, Me and $R_3$ represents H, $CH_2OH$, wherein the process steps comprising; stifling the olefin compound of general formula 1 wherein the value of R1, R2, R3 is same as mentioned for formula 2 and immobilized lipase enzyme with 2,3:4,6-di-O-isopropylidene-2-keto-L-gulonic acid monohydrate in a solvent at a temperature ranging between 20-30° C. at a pH ranging between 3-5, adding urea-hydrogen peroxide portion-wise to the said mixture, filtering the reaction mixture and evaporating the solvent from the filtrate followed by purification of the desired epoxide compound of general formula 2.

In an embodiment of the invention wherein the oxidizing agent used is 100% $H_2O_2$ in the form of adduct called urea-hydrogen peroxide (UHP).

In an embodiment of the invention wherein the enzyme immobilized lipase used is commercially available.

In an embodiment of the invention wherein the reaction is carried out in an aprotic solvent selected from a group consisting of dichloromethane, tetrahydrofuran and combination thereof, ionic liquid viz 1-butyl-3-methylimmidazolium bromide ([bmim]Br), fluorous solvent viz 1,1,1,3,3,3-hexafluoropropan-2-ol.

In an embodiment of the invention wherein the combination of solvent preferably used is dry dichloromethane or 20% THF in dichloromethane.

In an embodiment of the invention wherein the duration of the reaction is 20-30 hours.

In an embodiment of the invention wherein the yields of the products epoxide obtained ranges from 40-75% with enantiomeric excess (ee) of the products ranges from 35-71%.

In an embodiment of the invention wherein the product epoxide is separated from the catalyst by neutralizing the acid with sodium bicarbonate and isolating it in aqueous layer.

In an embodiment of the invention wherein the chiral acid 2,3:4,6-di-O-isopropylidene-2-keto-L-gulonic acid monohydrate is recycled for 5 times there is no appreciable loss of activity of the chiral acid used.

In an embodiment of the invention wherein the immobilized enzyme lipase is recycled for 5 times without any appreciable loss of activity, separating the granules by filtration and washing and drying.

Advantages of the present invention may include: it is a one-pot reaction; the system is recyclable and hence efficient and economic; the reaction condition is mild; and the method is eco-friendly.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Aspects of the Present Invention

The present invention relates to a novel chiral epoxidation of olefins using UHP and a chiral acid 2,3:4,6-di-O-isopropylidene-2-keto-L-gulonic acid monohydrate in presence of an immobilized lipase. As set forth in Scheme-1, the present invention relates to a method for preparation of chirally pure epoxide represented by the formula 2 and more particularly to a method which enables preparing optically pure R-(+)-4-hydroxy styrene oxide by oxidation of olefin with 2,3:4,6 di-O-isopropylidene-2-keto-gulonic acid monohydrate generated in situ by lipase catalysis in presence of urea-hydrogen peroxide oxidant at a pH range of 3-5.

Scheme 1

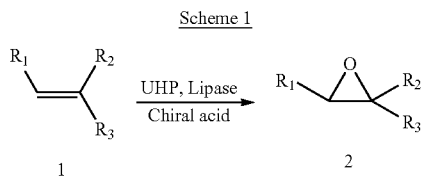

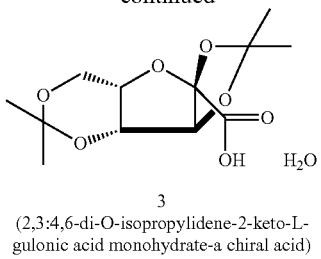

3
(2,3:4,6-di-O-isopropylidene-2-keto-L-
gulonic acid monohydrate-a chiral acid)

The present invention provides a method for chiral induction to epoxides represented by the formula '2' wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$ by 2,3:4,6 di-O-isopropylidene-2-keto-gulonic acid monohydrate of the formula '3' through lipase catalysed per-acid formation of it in presence of urea-hydrogen peroxide (UHP) as oxidizing agent in olefin of the formula '1' wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$.

Accordingly the present invention relates to a novel way for chiral epoxidation of the general structural formula '1' wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$. In one embodiment of the invention, representative compounds of the formula '1' are selected from the group wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$.

The invention also provides a process for the preparation of chirally pure epoxides of the structural formula '2', wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$ in which the process comprises relating substituted olefin with the per-acid generated in situ from 2,3:4,6-di-O-isopropylidene-2-keto-L-gulonic acid monohydrate and UHP under the catalytic influence of immobilized lipase.

In another embodiment of the invention, the reaction between olefin of the structural formula '1' and UHP under the catalytic influence of immobilized lipase (Novozyme [435]) is carried out in aprotic solvents selected from the group $CH_2Cl_2$, THF, $CH_2Cl_2$:THF (4:1), ionic liquid viz 1-butyl-3-methylimmidazolium bromide ([bmim]Br), fluorous solvent viz 1,1,1,3,3,3-hexafluoropropan-2-ol.

In another embodiment of the invention, the reaction between olefin and UHP is carried out in equimolar amount of the olefin represented by the structural formula '1' and UHP and catalytic amount of the chiral acid 2,3:4,6-di-O-isopropylidene-2-keto-L-gulonic acid monohydrate in presence of immobilized lipase.

In yet another embodiment of the invention, the reaction between olefin and UHP is carried out at a temperature range of 20-30° C. for a period of 15-30 hours.

In still yet another embodiment of the invention, the oxidant UHP is added portion-wise in 2 hours duration in order to avoid inhibition of the enzyme immobilized lipase. The yields and enantioselectivity obtained in the products have been found to be 40-75% and 35-71% respectively.

The details of the method disclosed in this invention have been described in the following examples which are provided to illustrate the invention only and therefore should not be construed to limit the scope of the present invention.

The present invention provides a novel method for chiral epoxidation of olefins of the general structural formula '1' wherein $R_1$ represents Me, Et, Ph, 4-(HO)$C_6H_4$, 3-(NO$_2$)$C_6H_4$, 4-(Cl)$C_6H_4$, $R_2$ represents H, Me and $R_3$ represents H, $CH_2OH$, CHO. Representative compounds of the structural formula '1' include styrene, 4-hydroxystyrene, 3-nitrostyrene, 4-chlorostyrene, trans-2-buten-1-ol, trans-2-methyl-pent-2-en-1-ol.

The process of preparation of the chiral epoxides of the structural formula '2' comprises stirring the olefin with urea hydrogen peroxide, immobilized lipase and 2,3:4,6-di-O-isopropylidene-2-keto-L-gulonic acid monohydrate in dichloromethane at a temperature in the range 20-30° C. for a period of 15-30 hours at a pH 3-5 until the completion of the reaction with occasional monitoring on TLC.

The reactions are also carried out in aprotic solvents such as THF, $CH_2Cl_2$:THF (4:1), ionic liquid viz 1-butyl-3-methylimmidazolium bromide ([bmim]Br) and fluorous solvent viz 1,1,1,3,3,3-hexafluoropropan-2-ol.

The sodium salt of the acid was regenerated by addition of dilute HCl and the chiral acid thus formed was isolated by extraction in ethyl acetate and dried. Then the solvent was removed under reduced pressure to get the chiral acid 2,3:4,6-di-O-isopropylidene-2-keto-L-gulonic acid monohydrate.

EXAMPLES

The following examples are given by way of illustrations and should not be construed to limit the scope of the invention. The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of 4-hydroxyphenyloxirane (in DCM:THF=4:1): 4-Hydroxy styrene (1 g, 8.3 mmol) was taken with 100 mg immobilized lipase and 2,3:4,6-di-O-isopropylidene-2-keto-L-gulonic acid monohydrate (0.3 g, 1.03 mmol) in dry dichloromethane:tetrahydrofuran (4:1) (15 mL) and stirred at 25° C. and added urea hydrogen peroxide (3 g, 32 mmol) portion-wise at pH 4 for 20 hours. The reaction was monitored occasionally on TLC. The mixture was filtered and washed the residue with dry dichloromethane:tetrahydrofuran (4:1) and the filtrate was reduced its volume under reduced pressure using vacuum flash evaporator. The chiral acid 2,3:4,6-di-O-isopropylidene-2-keto-L-gulonic acid monohydrate was recovered from the product by neutralizing it with sodium bicarbonate and isolated in water. The aqueous layer containing the sodium salt of the chiral acid was regenerated by adding dilute HCl solution and then extracted in ethyl acetate. Washed the ethyl acetate layer with fresh water, dried it and solvent was removed under reduced pressure to get 0.232 g of the chiral acid for recycling in the next run. The product was purified from the organic layer by preparative TLC in dry DCM:THF in 4:1 ratio. The residue containing the immobilized lipase and urea was washed with water for several times to remove the enzyme free from urea. It was then dried and the recovered amount collected was found to be 98 mg. The dried material (enzyme) was then kept for recycling. Yield of the product: 75%; oil (Found: C, 70.70; H, 5.91. $C_8H_8O_2$ requires C, 70.58; H, 5.88%); $R_f$ (90% $CH_2Cl_2$/EtOAc) 0.55. The enantiomeric excess was determined by HPLC analysis using a Chiralcel OD-R column [MeOH, flow rate 0.2 cm$^3$ min$^{-1}$], $[\alpha]_D^{25}$+4.95 (c 0.8, CHCl$_3$); ee 57%, R}; $\nu_{max}$ (neat/cm$^{-1}$) 3406, 2961, 2924, 2856, 1513, 1457; $\delta_H$ (300 MHz; CDCl$_3$) 2.0 (1H, b, HCOCHH), 2.2 (1H, b, HCOCHH), 3.4 (1H, b, CHOCH$_2$), 6.7-7.0 (4H, m, 4×CH, arom.); $\delta_C$ (300 MHz; CDCl$_3$) 26.4 (CH$_2$), 48.13 (CH), 115.5, 128.2, 137.3, 154.2 (6×C-Ph). MS m/z (rel. intensity %): 136 [M$^+$].

Recycling of Immobilized Lipase

1(a): First recycling: Recovered immobilized lipase (98 mg), fresh chiral acid 2,3:4,6-di-O-isopropylidene-2-keto-L-gulonic acid monohydrate (0.3 g), 4-hydroxy styrene (1 g, 8.3 mmol) were taken in 15 mL dry dichloromethane:tetrahydrofuran (4:1) and to it was added urea hydrogen peroxide (3 g, 32 mmol) portion-wise at pH 4 and stirred at 25° C. for 20 hours. Separation of the product 4-hydroxyphenyloxirane and recovery of the enzyme were done in an analogous manner as given in 'example 1' for use in the subsequent recycles. Yield: 73%.

1(b): Second recycling: 4-Hydroxy styrene: 1 g, 8.3 mmol, urea hydrogen peroxide: 3 g, 32 mmol, Immobilized lipase: 96 mg, 2,3:4,6-di-O-isopropylidene-2-keto-L-gulonic acid monohydrate: 0.3 g, 1.03 mmol, dry dichloromethane:tetrahydrofuran (4:1): 15 mL. Same procedure was followed as described in example '1'. Reaction time: 20 hours, Yield: 71%.

1(c): Third recycling: 4-Hydroxy styrene: 1 g, 8.3 mmol, urea hydrogen peroxide: 3 g, 32 mmol, Immobilized lipase: 93 mg, 2,3:4,6-di-O-isopropylidene-2-keto-L-gulonic acid monohydrate: 0.3 g, 1.03 mmol, dry dichloromethane:tetrahydrofuran (4:1): 15 mL. Same procedure was followed as described in example '1'. Reaction time: 20 hours, Yield: 70%.

1(d): Fourth recycling: 4-Hydroxy styrene: 1 g, 8.3 mmol, urea hydrogen peroxide: 3 g, 32 mmol, Immobilized lipase: 90 mg, 2,3:4,6-di-O-isopropylidene-2-keto-L-gulonic acid monohydrate: 0.3 g, 1.03 mmol, dry dichloromethane:tetrahydrofuran (4:1): 15 mL. Same procedure was followed as described in example '1'. Reaction time: 20 hours, Yield: 68%.

1(e): Fifth recycle 4-Hydroxy styrene: 1 g, 8.3 mmol, urea hydrogen peroxide: 3 g, 32 mmol, Immobilized lipase: 87 mg, 2,3:4,6-di-O-isopropylidene-2-keto-L-gulonic acid monohydrate: 0.3 g, 1.03 mmol, dry dichloromethane:tetrahydrofuran (4:1): 15 mL. Same procedure was followed as described in example '1'. Reaction time: 20 hours, Yield: 66%.

Recycling of 2,3:4,6-di-O-isopropylidene-2-keto-L-gulonic acid monohydrate (chiral acid)

1(a): First recycle: 4-Hydroxy styrene: 1 g, 8.3 mmol, urea hydrogen peroxide: 3 g, 32 mmol, Immobilized lipase: 100 mg, 2,3:4,6-di-O-isopropylidene-2-keto-L-gulonic acid monohydrate: 0.292 g (recovered from example 1), 1.00 mmol, dry dichloromethane:tetrahydrofuran (4:1): 15 mL. Same procedure was followed as described in example '1'. Reaction time: 20 hours, Yield: 74%.

1(b): Second recycle: 4-Hydroxy styrene: 1 g, 8.3 mmol, urea hydrogen peroxide: 3 g, 32 mmol, Immobilized lipase: 100 mg, 2,3:4,6-di-O-isopropylidene-2-keto-L-gulonic acid monohydrate: 0.286 g, 0.97 mmol, dry dichloromethane:tetrahydrofuran (4:1): 15 mL. Same procedure was followed as described in example '1'. Reaction time: 20 hours, Yield: 72%.

1(c): Third recycle: 4-Hydroxy styrene: 1 g, 8.3 mmol, urea hydrogen peroxide: 3 g, 32 mmol, Immobilized lipase: 100 mg, 2,3:4,6-di-O-isopropylidene-2-keto-L-gulonic acid monohydrate: 0.272 g, 0.93 mmol, dry dichloromethane:tetrahydrofuran (4:1): 15 mL. Same procedure was followed as described in example '1'. Reaction time: 20 hours, Yield: 71%.

1(d): Fourth recycle: 4-Hydroxy styrene: 1 g, 8.3 mmol, urea hydrogen peroxide: 3 g, 32 mmol, Immobilized lipase: 100 mg, 2,3:4,6-di-O-isopropylidene-2-keto-L-gulonic acid monohydrate: 0.263 g, 0.90 mmol, dry dichloromethane:tetrahydrofuran (4:1): 15 mL. Same procedure was followed as described in example '1'. Reaction time: 20 hours, Yield: 68%.

1(e): Fifth recycle: 4-Hydroxy styrene: 1 g, 8.3 mmol, urea hydrogen peroxide: 3 g, 32 mmol, Immobilized lipase: 100 mg, 2,3:4,6-di-O-isopropylidene-2-keto-L-gulonic acid monohydrate: 0.254 g, 0.87 mmol, dry dichloromethane:tetrahydrofuran (4:1): 15 mL. Same procedure was followed as described in example '1'. Reaction time: 20 hours, Yield: 67%.

Example 2

Preparation of 4-hydroxyphenyloxirane (in dry DCM): 4-Hydroxy styrene: 1 g, 8.3 mmol, urea hydrogen peroxide: 3 g, 32 mmol, immobilized lipase: 100 mg, 2,3:4,6-di-O-isopropylidene-2-keto-L-gulonic acid monohydrate: 0.3 g, 1.03 mmol, dry dichloromethane: 15 mL. Same procedure was followed as described in example '1'. Reaction time: 30 hours, Yield: 60%, $[\alpha]_D^{25}$: +4.78 (c 0.9, CHCl$_3$); ee 55%, R.

Example 3

Preparation of 4-hydroxyphenyloxirane (in dry THF): 4-Hydroxy styrene: 1 g, 8.3 mmol, urea hydrogen peroxide: 3 g, 32 mmol, immobilized lipase: 100 mg, 2,3:4,6-di-O-isopropylidene-2-keto-L-gulonic acid monohydrate: 0.3 g, 1.03 mmol, dry tetrahydrofuran: 15 mL. Same procedure was followed as described in example '1'. Reaction time: 30 hours, Yield: 48%, $[\alpha]_D^{25}$: +4.60 (c 0.6, CHCl$_3$); ee 53%, R.

Example 4

Preparation of 4-hydroxyphenyloxirane (in fluorous solvent): 4-Hydroxy styrene: 1 g, 8.3 mmol, urea hydrogen peroxide: 3 g, 32 mmol, immobilized lipase: 100 mg, 2,3:4,6-di-O-isopropylidene-2-keto-L-gulonic acid monohydrate: 0.3 g, 1.03 mmol, 1,1,1,3,3,3-hexafluoropropan-2-ol: 15 mL. Same procedure was followed as described in example '1'. Reaction time: 30 hours, Yield: 45%, $[\alpha]_D^{25}$: +4.34 (c 0.6, CHCl$_3$); ee 50%, R.

Example 5

Preparation of 4-hydroxyphenyloxirane (in ionic liquid): 4-Hydroxy styrene: 1 g, 8.3 mmol, urea hydrogen peroxide: 3 g, 32 mmol, immobilized lipase: 100 mg, 2,3:4,6-di-O-isopropylidene-2-keto-L-gulonic acid monohydrate: 0.3 g, 1.03 mmol, 1-butyl-3-methylimmidazolium bromide (bmimBr): 15 mL. Same procedure was followed as described in example '1'. Reaction time: 30 hours, Yield: 40%, $[\alpha]_D^{25}$: +4.43 (c 0.6, CHCl$_3$); ee 51%, R.

Example 6

Preparation of 4-hydroxyphenyloxirane using aqueous hydrogen peroxide: 4-Hydroxy styrene: 1 g, 8.3 mmol, aqueous hydrogen peroxide (30%): 3.4 mL, 30 mmol, immobilized lipase: 100 mg, 2,3:4,6-di-O-isopropylidene-2-keto-L-gulonic acid monohydrate: 0.3 g, 1.03 mmol, dry dichloromethane: 15 mL. Same procedure was followed as described in example '1'. Reaction time: 30 hours, Yield: 10%, $[\alpha]_D^{25}$: +0.65 (c 0.6, CHCl$_3$); ee 7.5%, R.

Example 7

Preparation of 2,3-epoxy-2-methylpentanol: 2-Methylpenten-2-ol (1 g, 10 mmol) was taken with 100 mg Immobilized lipase and 2,3:4,6-di-O-isopropylidene-2-keto-L-gulonic acid monohydrate (0.3 g, 1.03 mmol) in dry dichloromethane (15 mL) and stirred at 30° C. and added urea hydrogen peroxide (3 g, 32 mmol) portion-wise at pH 5 for 20 hours. The reaction was monitored occasionally on TLC. The mixture was filtered and washed the residue with dichloromethane and the filtrate was reduced its volume under reduced pressure using vacuum flash evaporator. The product was purified by preparative TLC with 30% EtOAc/hexane. Yield: 70%; oil (Found: C, 62.01; H, 10.65. $C_6H_{12}O_2$ requires C, 62.07; H, 10.34%); R$_f$ (30% EtOAc/hexane) 0.65. The enantiomeric excess was determined by HPLC analysis using a Chiralcel OD-R column [MeOH, flow rate 0.5 cm$^3$ min$^{-1}$], $[\alpha]_D^{25}$+4.33 (c 0.03, CHCl$_3$) 71% ee; {lit., $[\alpha]_D^{24}$ 5.8 (c 0.36, CHCL$_3$), 95% ee}; $\nu_{max}$ (neat/cm$^{-1}$) 3407, 2963, 2932, 2875, 1457, 1376; $\delta_H$ (300 MHz; CDCl$_3$) 0.96 (3H, t, CH$_2$CH$_3$), 1.31 (3H, S, OCCH$_3$), 1.46 (2H, m, OCHCH$_2$CH$_3$), 2.0 (1H, b, OH), 2.51 (1H, t, OCHCH$_2$), 3.5-3.7 (2H, m, CCH$_2$OH); $\delta_C$ (300 MHz; CDCl$_3$) 11.O (CH$_3$CH$_2$), 14.5 (CH$_3$CO), 21.6 (CH$_2$CH$_2$), 61.7 (CH$_2$CHO), 62.8 (CH$_3$CO), 70.3 (CH$_2$OH). MS m/z (rel. intensity %): 116 [M$^+$]

Example 8

Preparation of 2,3-epoxybutan-1-ol: But-2-en-1-ol (1 g, 13.9 mmol) was taken with 100 mg Immobilized lipase and 2,3:4,6-di-O-isopropylidene-2-keto-L-gulonic acid monohydrate (0.3 g, 1.03 mmol) in dry dichloromethane (15 mL) and stirred at 30° C. and added urea hydrogen peroxide (3 g, 32 mmol) portion-wise at pH 5 for 20 hours. The reaction was monitored occasionally on TLC. The mixture was filtered and washed the residue with dichloromethane and the filtrate was reduced its volume under reduced pressure using vacuum flash evaporator. The product was purified by preparative TLC with 70% EtOAc/hexane. Yield: 65%; oil (Found: C, 54.2; H, 9.2. $C_4H_8O_2$ requires C, 54.5; H, 9.09%); R$_f$ (70% EtOAc/hexane) 0.45. The enantiomeric excess was determined by HPLC analysis using a Chiralcel OD-R column [MeOH, flow rate 0.5 cm$^3$ min$^{-1}$], $[\alpha]_D^{25}$+19.33 (c 0.05, CHCl$_3$) 35% ee; {lit., $[\alpha]_D^{24}$+55.0 (c 0.36, CHCL$_3$), 95% ee}; $\nu_{max}$ (neat/cm$^{-1}$) 3399, 2957, 2924, 2853, 1464, 1378; $\delta_H$ (300 MHz; CDCl$_3$) 1.2 (3H, d, CH$_3$CHO), 2.1 (1H, b, CH$_2$OH), 2.6 (1H, m, OHCH$_2$CHO), 2.7 (1H, m, CH$_3$CHO), 3.7 (2H, m, OCHCH$_2$OH); $\delta_C$ (75 MHz; CDCl$_3$) 16.2 (CH$_3$CHO), 46.5 (CH$_3$CHO), 62.0 (HOCH$_2$CHO), 64.3 (CH$_2$OH). MS m/z (rel. intensity %): 88 [M$^+$]

Example 9

Preparation of phenyloxirane: Styrene (1 g, 9.6 mmol) was taken with 100 mg Immobilized lipase and 2,3:4,6-di-O-isopropylidene-2-keto-L-gulonic acid monohydrate (0.3 g, 1.03 mmol) in dry dichloromethane (15 mL) and stirred at 25° C. and added urea hydrogen peroxide (3 g, 32 mmol) portion-wise at a pH 5 for 20 hours. The reaction was monitored occasionally on TLC. The mixture was filtered and washed the residue with dichloromethane and the filtrate was reduced its volume under reduced pressure using vacuum flash evaporator. The product was purified by preparative TLC with 40% CH$_2$Cl$_2$/hexane. Yield: 70%; oil (Found: C, 79.91; H, 6.65. $C_8H_8O$ requires C, 79.97; H, 6.71%); R$_f$ (40% CH$_2$Cl$_2$/hexane) 0.55. The enantiomeric excess was determined by HPLC analysis using a Chiralcel OD column [$^i$PrOH:hexane=0.2: 99.8, flow rate 0.2 cm$^3$ min$^{-1}$], $[\alpha]_D^{22}$+21.6 (c 0.7, PhH) 48% ee; {lit., $[\alpha]_D^{22}$+44.8 (c 1.00, PhH), R}; $\nu_{max}$ (neat/cm$^{-1}$) 1496, 1476, 1452, 1390; $\delta_H$ (300 MHz; CDCl$_3$) 2.80 (1H, dd, J 2.6 and 5.5, HCOCHH), 3.13 (1H, dd, J 4.1 and 5.5, HCO-CHH), 3.85 (1H, dd, J 2.6 and 4.0, PhCHOCH$_2$), 7.26-7.36 (5H, m, 5×CH, arom.); $\delta_C$ (300 MHz; CDCl$_3$) 51.7 (CH$_2$), 52.8 (CH), 125.9, 126.3, 128.6, 128.9 and 138.0 (6×C-Ph). MS m/z (rel. intensity %): 122 (M+2, 15), 121 (M+1, 43), 120 (M$^+$, 20), 105(100), 91(68), 77 (88).

Example 10

Preparation of (3-Nitrophenyl)oxirane: 3-Nitrostyrene (1 g, 6.71 mmol) was taken with 100 mg Immobilized lipase and 2,3:4,6-di-O-isopropylidene-2-keto-L-gulonic acid monohydrate (0.3 g, 1.03 mmol) in dry dichloromethane (15 mL) and stirred at 25° C. and added urea hydrogen peroxide (3 g, 32 mmol) portion-wise at a pH 5 for 20 hours. The reaction was monitored occasionally on TLC. The mixture was filtered and washed the residue with dichloromethane and the filtrate was reduced its volume under reduced pressure using vacuum flash evaporator. The product was purified by preparative TLC with 25% EtOAc/hexane. 75% Yield; Yellow oil (Found: C, 58.22; H, 4.28; N, 8.50. $C_8H_7NO_3$ requires C, 58.18; H, 4.27; N, 8.48%); R$_f$ (25% EtOAc/hexane) 0.50; $[\alpha]_D^{20}$−1.51 (c 2.0, CHCl$_3$); {lit., $[\alpha]_D^{18}$+2.5 (c 2.8, CHCl$_3$, S}; HPLC analysis using a Chiralpak AD column showed it to be 60% ee [hexane: 2-propanol=9:1, flow rate 0.8 cm$^3$ min$^{-1}$]; $\nu_{max}$ (neat/cm$^{-1}$) 3113, 2995, 1517, 1343, 1301, 1042, 983, 888, 788, 740; $\delta_H$ (300 MHz; CDCl$_3$) 2.80 (1H, dd, J 2.5 and 4.8, HCOCHH), 3.21 (1H, dd, J 3.9 and 4.8, HCOCHH), 3.97 (1H, dd, J 2.5 and 3.9, PhCHOCH$_2$), 7.40-7.75 (2H, m, 2×CH, arom.) and 8.01-8.24 (2H, m, 2×CH, arom.); $\delta_C$ (300 MHz; CDCl$_3$) 51.7 (CH$_2$), 51.9 (CH), 126.0, 126.4, 145.4 and 148.6 (6×C-Ph); MS m/z (rel. intensity %): 165 (M$^+$, 18), 150(32), 136(68), 120(25), 105(17), 90(100), 77(22), 74(12), 65(52), 63 (59).

Example 11

Preparation of (4-Chlorophenyl)oxirane: 4-Chlorostyrene (1 g, 7.22 mmol) was taken with 100 mg Immobilized lipase and 2,3:4,6-di-O-isopropylidene-2-keto-L-gulonic acid monohydrate (0.3 g, 1.03 mmol) in dry dichloromethane (15 mL) and stirred at 25° C. and added urea hydrogen peroxide (3 g, 32 mmol) portion-wise at a pH 5 for 20 hours. The reaction was monitored occasionally on TLC. The mixture was filtered and washed the residue with dichloromethane and the filtrate was reduced its volume under reduced pressure using vacuum flash evaporator. The product was purified by preparative TLC with 40% EtOAc/hexane. 73% Yield; oil (Found: C, 62.11; H, 4.51. $C_8H_7OCl$ requires C, 62.09; H, 4.53%); R$_f$ (40% EtOAc/hexane) 0.51; $[\alpha]_D^{22}$-13.4 (c 1.00, CHCl$_3$); {lit., $[\alpha]_D^{20}$−24.0 (c 1.08, CHCl$_3$), 97% ee, R}; HPLC analysis using a Chiralcel OJ column showed it to be 54% ee [hexane: 2-propanol=9:1, flow rate 0.8 cm$^3$ min$^{-1}$];

$\nu_{max}$ (neat/cm$^{-1}$) 3054, 2992, 2920, 1602, 1496, 1478, 1417, 1381, 1199, 1090, 1015, 987, 879, 831, 769; $\delta_H$ (300 MHz; CDCl$_3$) 2.68-2.69 (1H, dd, J 2.6 and 5.4, HCOCHH), 3.08 (1H, dd, J 4.0 and 5.4, HCOCHH), 3.77 (1H, dd, J 2.6 and 4.0, PhCHOCH$_2$), 7.13-7.26 (4H, m, 4×CH, arom.); $\delta_C$ (300 MHz; CDCl$_3$) 51.2 (CH$_2$), 51.8 (CH), 126.7, 126.6, 133.9 and 136.1 (6×C-Ph). MS m/z (rel. intensity %): 156, 154 (M+1, 2, 8), 155, 153 (M$^+$, 3, 7), 138(3), 125(40), 119(39), 91(29), 89(100), 63(34), 50 (17).

The sodium salt of the acid was regenerated by addition of dilute HCl and the chiral acid thus formed was isolated by extraction in ethyl acetate and dried. Then the solvent was removed under reduced pressure to get the chiral acid 2,3:4,6-di-O-isopropylidene-2-keto-L-gulonic acid monohydrate.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for preparation of chiral epoxy compounds of general formula 2

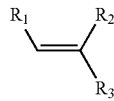

1

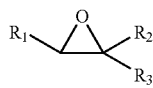

2 wherein R$_1$ represents Me, Et, Ph, 4-(HO)C$_6$H$_4$, 3-(NO$_2$)C$_6$H$_4$, 4-(Cl)C$_6$H$_4$, R$_2$ represents H, Me and R$_3$ represents H, CH$_2$OH, wherein the process steps comprise: stifling the olefin compound of general formula 1 wherein the value of R1, R2, R3 is same as mentioned for formula 2 and immobilized lipase enzyme with 2,3:4,6-di-O-isopropylidene-2-keto-L-gulonic acid monohydrate in a solvent at a temperature ranging between 20-30° C. at a pH ranging between 3-5, adding urea-hydrogen peroxide adduct as an oxidizing agent portion-wise to the said mixture, filtering the reaction mixture and evaporating the solvent from the filtrate followed by purification of the desired epoxide compound of general formula 2.

2. The method of claim 1, wherein the urea-hydrogen peroxide adduct (UHP) used has 100% H$_2$O$_2$.

3. The method of claim 1, wherein the enzyme immobilized lipase used is commercially available.

4. The method of claim 1, wherein the reaction is carried out in an aprotic solvent selected from a group consisting of dichloromethane, tetrahydrofuran and combination thereof, ionic liquid viz 1-butyl-3-methylimmidazolium bromide ([bmim]Br), fluorous solvent viz 1,1,1,3,3,3-hexafluoropropan-2-ol.

5. The method of claim 1, wherein the solvent used is dry dichloromethane or 20% THF in dichloromethane.

6. The method of claim 1, wherein the duration of the reaction is 20-30 hours.

7. The method of claim 1, wherein the yields of the products epoxide obtained up to 75% with enantiomeric excess (ee) of the products up to 35-71%.

8. The method of claim 1, wherein the product epoxide is separated from the catalyst by neutralizing the acid with sodium bicarbonate and isolating it in aqueous layer.

9. The method of claim 1, wherein the chiral acid 2,3:4,6-di-O-isopropylidene-2-keto-L-gulonic acid monohydrate is recycled 5 times with no appreciable loss of activity of the chiral acid used.

10. The method of claim 1, wherein the immobilized enzyme lipase is recycled 5 times without any appreciable loss of activity, and further comprising separating the granules by filtration and washing and drying.

* * * * *

UNITED STATES PATENT AND TRADEMARK OFFICE
CERTIFICATE OF CORRECTION

| | |
|---|---|
| PATENT NO. | : 8,148,118 B2 |
| APPLICATION NO. | : 12/626843 |
| DATED | : April 3, 2012 |
| INVENTOR(S) | : Amrit Goswami et al. |

Page 1 of 1

It is certified that error appears in the above-identified patent and that said Letters Patent is hereby corrected as shown below:

In claim 1, column 20, line 3, delete "stifling" and insert --stirring-- therefor.

Signed and Sealed this
Twenty-ninth Day of May, 2012

David J. Kappos
*Director of the United States Patent and Trademark Office*